United States Patent [19]
Dehlinger

[11] Patent Number: 5,723,320
[45] Date of Patent: Mar. 3, 1998

[54] POSITION-ADDRESSABLE POLYNUCLEOTIDE ARRAYS

[76] Inventor: Peter J. Dehlinger, 58 Roosevelt Cir., Palo Alto, Calif. 94306

[21] Appl. No.: 520,730

[22] Filed: Aug. 29, 1995

[51] Int. Cl.$^6$ .............................. C12P 19/34; C12Q 1/68; C12Q 1/70; C07H 21/04

[52] U.S. Cl. .............................. 435/91.1; 435/5; 435/91.2; 536/24.3; 536/24.33; 536/24.32

[58] Field of Search .................................. 435/6, 5, 91.2, 435/91.1; 536/24.3–24.33

[56] References Cited

FOREIGN PATENT DOCUMENTS

WO 94/11530  5/1994  WIPO.
WO 95/00530  1/1995  WIPO.

OTHER PUBLICATIONS

Fodor et al. Science 251:767–773, Feb. 15, 1991.

*Primary Examiner*—W. Gary Jones
*Assistant Examiner*—Dianne Rees
*Attorney, Agent, or Firm*—Peter J. Dehlinger

[57] ABSTRACT

A method for producing a high-density, position-addressable gene array is disclosed. The method includes contacting an array of different-sequence oligonucleotides having a unique, known combinatorial sequence associated with each position in the array with a set of extended gene probe templates which are complementary to the oligonucleotides at one of the template end regions. After hybridization, the oligonucleotides in the array are extended by strand-directed polymerization to form the probe array. Also disclosed is a probe array device formed by the method.

13 Claims, 6 Drawing Sheets

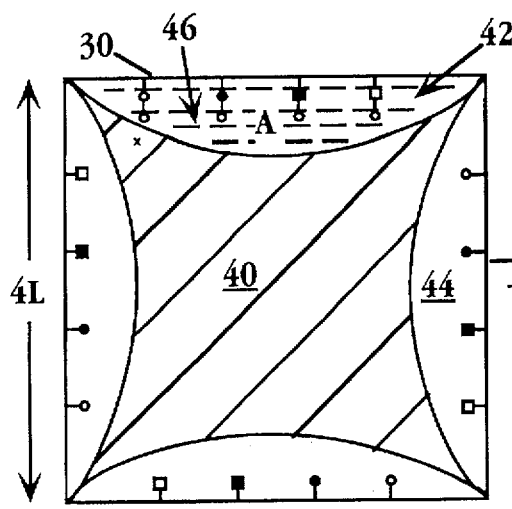
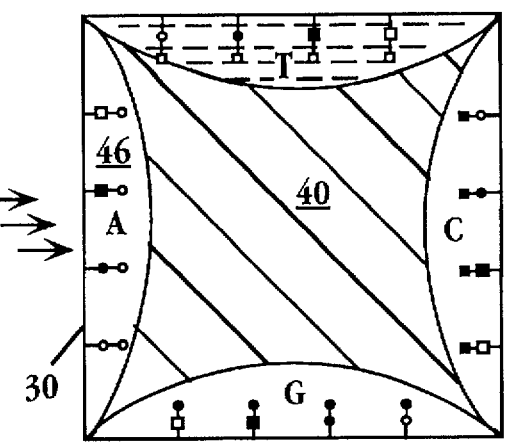
Fig. 4A    Fig. 4B
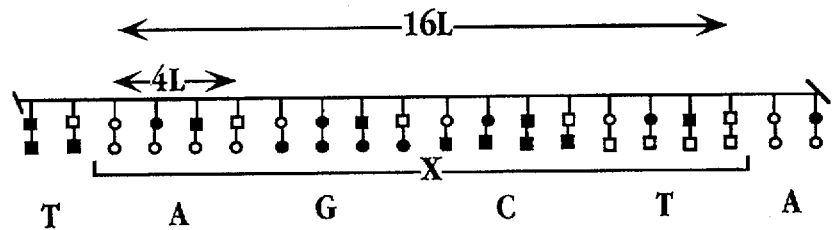
Fig. 5
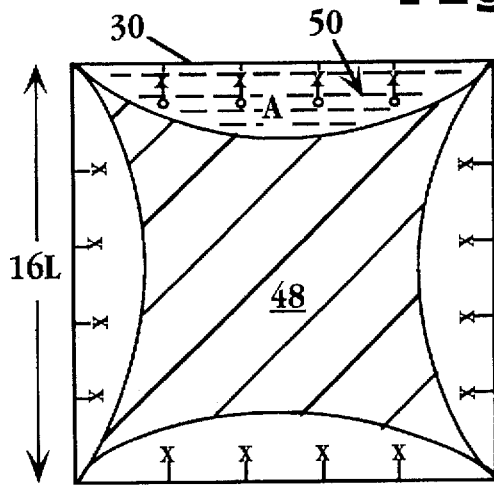
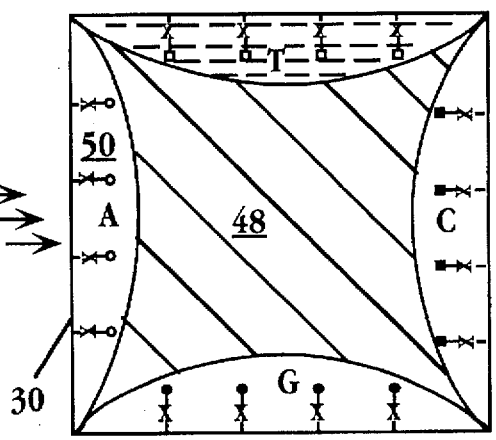
Fig. 6A    Fig. 6B
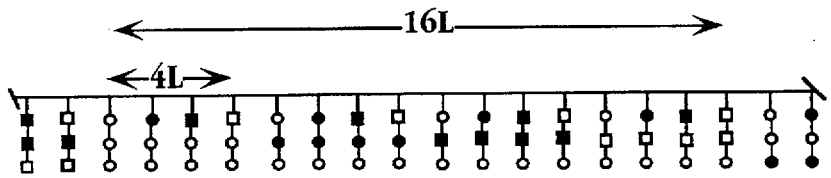
Fig. 7

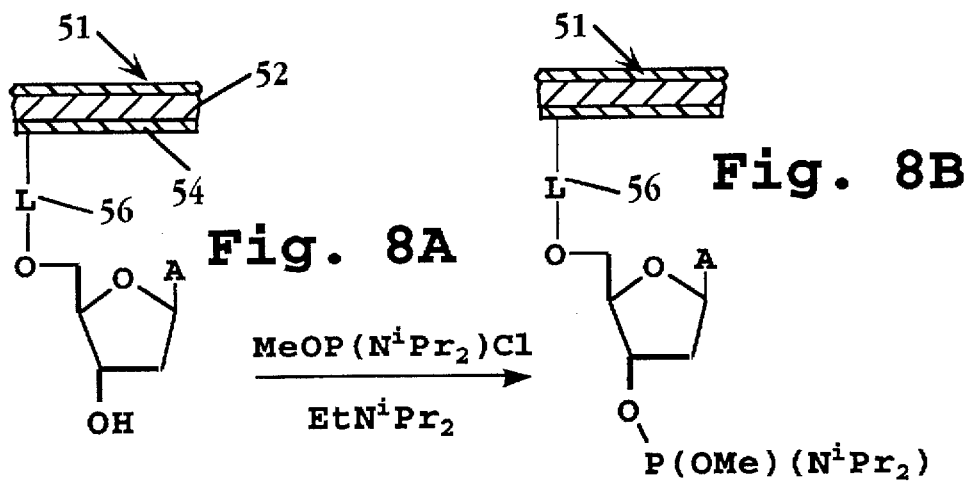
Fig. 8A
Fig. 8B
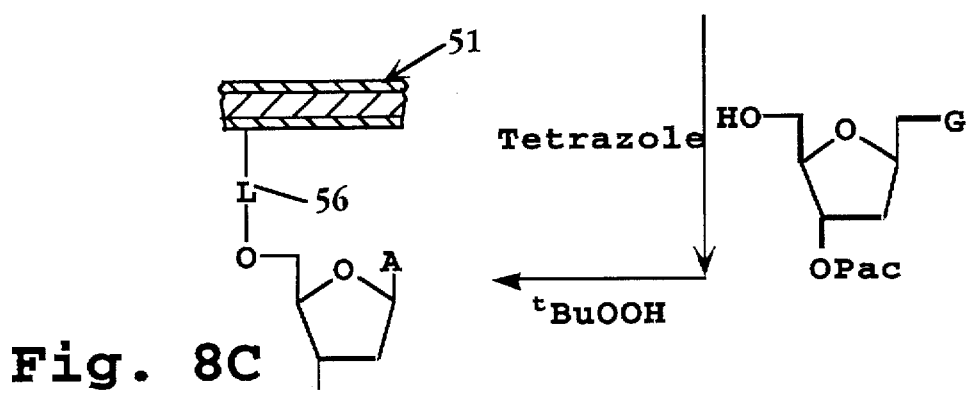
Fig. 8C
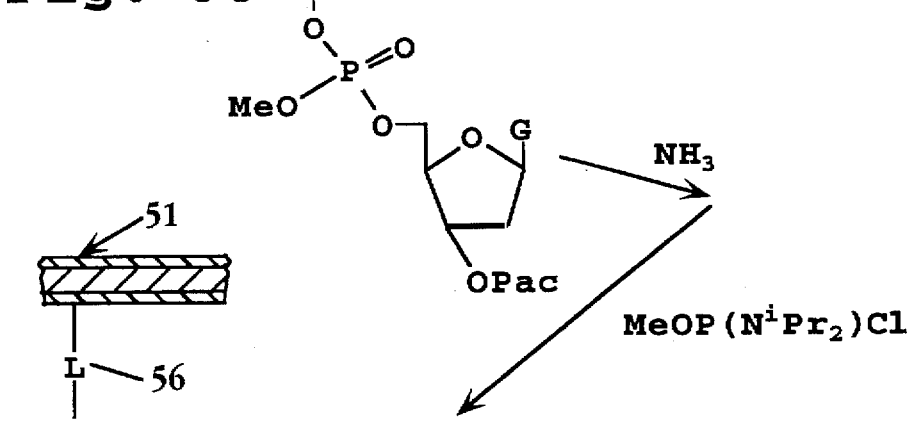
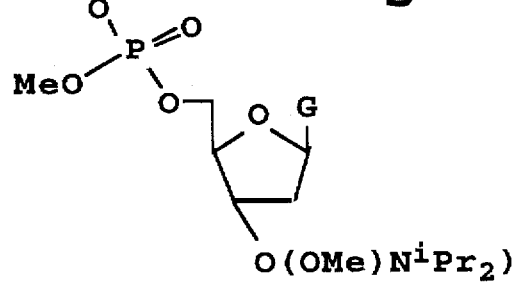
Fig. 8D

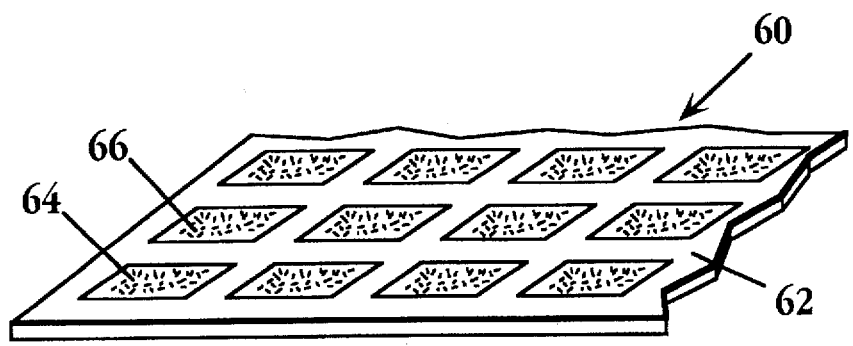
Fig. 9
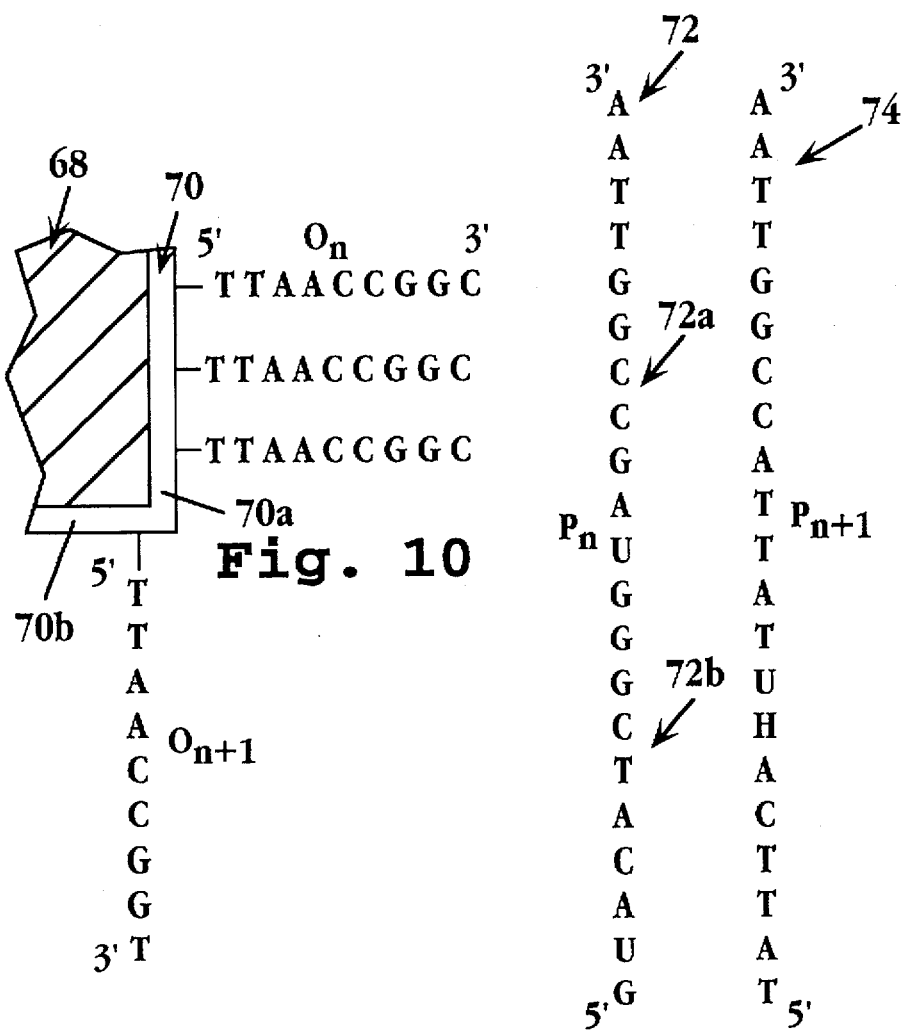
Fig. 10
Fig. 11

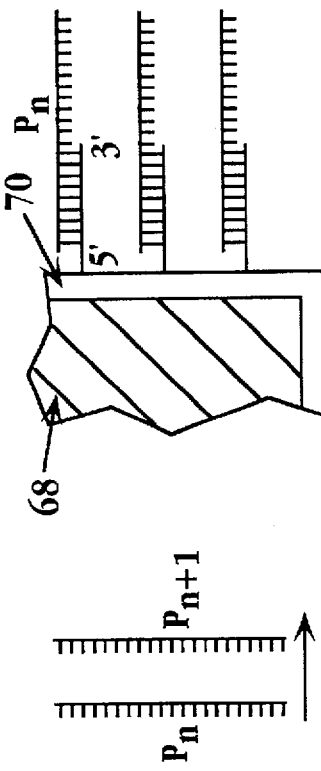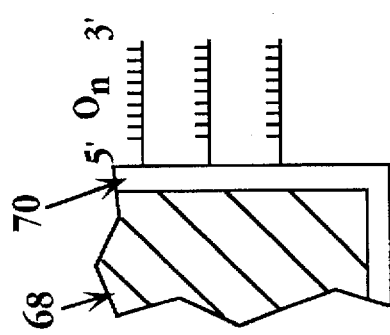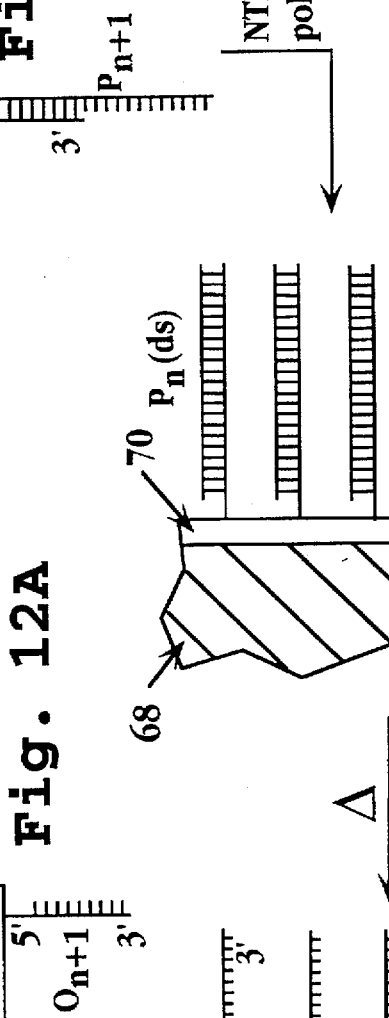
Fig. 12A
Fig. 12B
Fig. 12C
Fig. 12D

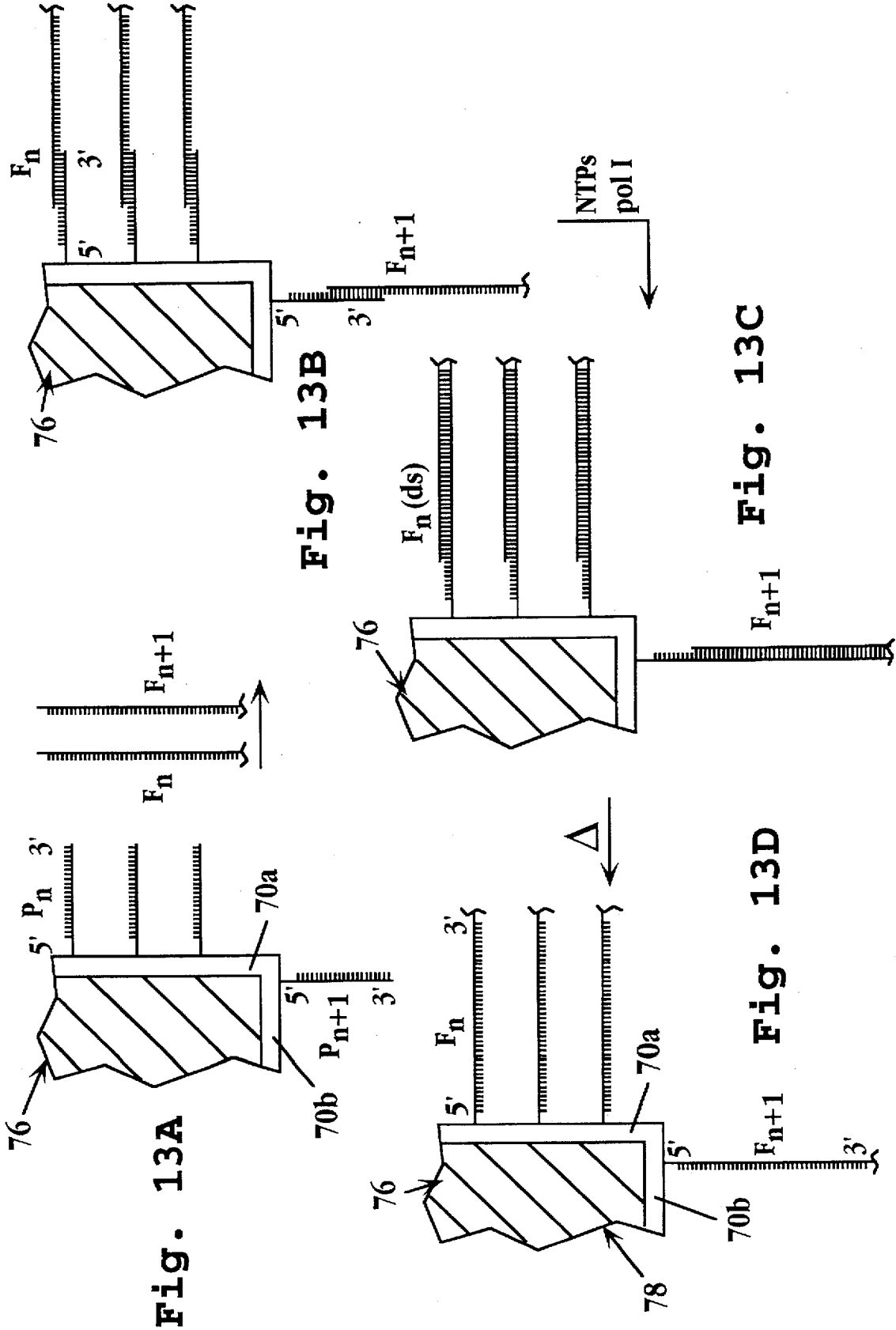

POSITION-ADDRESSABLE POLYNUCLEOTIDE ARRAYS

FIELD OF THE INVENTION

The present invention relates to a method for forming position-addressable polynucleotide arrays, such as arrays of known-sequence genes or gene probes.

REFERENCES

Chu, T. J., et al., *Electrophoresis* 13:105–114 (1992).

Coeling, K. J., in *KIRK-OTHMER ENCYCLOPEDIA OF CHEMICAL TECHNOLOGY*, 3rd ed., John Wiley & Sons, New York, Vol. 6, 661–669.

Fodor, S. P. A., et al., *Science* 251:767–773 (1991).

Gait, M. J., ed., *OLIGONUCLEOTIDE SYNTHESIS: A PRACTICAL APPROACH*, Oxford Univ. Press, 1990.

Hames, B. D., et al., *NUCLEIC ACID HYBRIDIZATION*, IRL Press (1985).

Lee, S. M., in *ENCYCLOPEDIA OF POLYMER SCIENCE AND ENGINEERING*, 2nd ed., Vol. 3, John Wiley & Sons, New York, 601–615.

Matson, R. S. et al., *Anal. Biochem.* 217: 306–310 (1994).

Matson, R. S. et al., *Anal. Biochem.* 224:110–116 (1995).

Pirrung, et al., U.S. Pat. No. 5,143,854 (1992).

Pirrung, M. C., et al., U.S. Pat. No. 5,143,854

Sambrook, J., et al., in *MOLECULAR CLONING: A LABORATORY MANUAL*, 2nd Edition, Cold Spring Harbor Lab Press (1989).

Southern, E., EP Patent No. 373,203 (1994).

Southern, E. et al., *Genomics* 13:1008–1017 (1992).

Virnekas, B., et al., *Nuc. Acids Res.* 22(25):5600 (1994).

BACKGROUND OF THE INVENTION

There is widespread interest in gene probe and gene arrays, for example, (i) for use in gene-based diagnostics aimed at detecting one of a number of possible mutations in a given gene, (ii) for identifying genomic or cDNA library species associated with one or more given RNA species, and (iii) for gene expression studies.

Heretofore, arrays of genes, e.g., cDNAs or genomic library clones, have been formed by spotting individual genes on suitable substrates, e.g., nitrocellulose filter paper, for subsequent blotting, e.g., with radiolabeled probes. This approach is relatively labor-intensive, requiring that each gene be individually spotted on the substrate. The approach is also limited in array-region density to the physical resolution achievable by the device used for spotting.

More recently, a method for preparation of high density position-addressable oligomer arrays on a planar substrate has been reported (Fodor, Pirrung). In this method a substrate having photoprotective groups is irradiated in selected regions only, using photolithographic mask techniques, to deprotect surface active groups in those selected regions. The entire surface is then treated with a solution of a selected subunit, which itself has a photoprotected group, to react this subunit with the surface groups in the photodeprotected regions. This process is repeated to (i) add a selected subunit at each region of the surface, and (ii) build up different-sequence oligomers at known, addressable regions of the surface.

This method has the advantage that reaction sites do not have to be physically separated during subunit addition, and therefore massive parallel subunit addition is possible by applying subunit-addition reagents over the entire surface of the array. Greater site density is therefore feasible than in systems where physical separation of reagents is required from one reaction site to another, and where individual reagents are spotted or deposited in defined array regions.

Co-owned patent application Ser. No. 08/512,027 for Method and Apparatus for Producing Position-Addressable Combinatorial Libraries, filed Aug. 7, 1995, discloses another method for producing position-addressable, high-density arrays of oligomers. The approach involves forming a one-dimensional position-addressable array of oligomers on a filament, by a series of subunit addition reactions in which each of a plurality of subunits is reacted with different segments of the filament wound on a spool, where successive subunit reactions are carried out on successively smaller-diameter (or larger-diameter) spools.

Like the two-dimensional photo-masking techniques, the one-dimensional filament-spool method just outline employs massive parallel subunit synthesis to efficiently produce high-density arrays of position-addressable oligomers, e.g., oligonucleotides. Thus, for example, to form a hexamer array of $4^6$ oligonucleotides, only four addition reactions are required at each subunit addition step (one for each of the four nucleotides), so that the total $4^6$ array can be produced in 4×6=24 reactions. By contrast, if each subunit were added separately to each array region, a total of $4^6$ separate subunit addition steps would be required (as, for example, proposed by Southern).

The direct use of massive parallel subunit addition, for synthesis of position-addressable oligomer libraries, is not readily adaptable to the synthesis of position-addressable gene arrays for two reasons. First, since the gene sequences are expected to be random rather than combinatorial, there is no simple way of patterning the genes on a substrate so that the unique gene sequences can be built up by massive parallel step-wise synthesis. Secondly, good gene-sequence fidelity would be obtainable in high-density arrays only up to about 6–10 subunits, whereas genes or gene probes of interest will typically contain 15–100 or more nucleotides.

It would therefore be useful to provide a method of forming high-density, position-addressable arrays of genes or gene probes which can be produced in a way that takes advantage of the massive parallel synthesis methods just outlined, but which is not constrained by the limitations just discussed.

SUMMARY OF THE INVENTION

The invention includes, in one aspect, a method of producing a position-addressable array of known-sequence gene probes. The method employs an array of different-sequence oligonucleotides, where each oligonucleotide in the array has a unique, known combinatorial sequence associated with a known-address region in the array. This array is preferably a combinatorial oligonucleotide array of the type described above, produced by massive parallel subunit addition methods.

The array is contacted with a set of gene-probe templates, where each member of the set has a probe segment whose sequence is complementary to a selected, known-sequence gene probe and a recognition segment whose nucleotide sequence is complementary to one of the array oligonucleotides. The contacting is carried out under complementary-strand hybridization conditions, such that each member in the template set becomes hybridized, through its recognition segment, to a complementary-sequence oligonucleotide in the array of oligonucleotides.

The oligonucleotide probes in the array are then extended, by strand-directed polymerization, along the probe segments of the templates hybridized to the oligonucleotides, to produce the desired probe array.

The probe segments in the set of gene-probe templates are preferably at least 10–15 nucleotide bases in length, and may be up to several hundred bases. The oligonucleotides forming the array library preferably form a combinatorial library of different-sequence oligonucleotides having a selected length of typically 3 and 8 subunits.

In one general embodiment, the position-addressable array of different-sequence oligonucleotides is formed on a wound or extended filament having a one-dimensional array of regions, each carrying a different-sequence oligonucleotide in said combinatorial library. The linear density of the oligonucleotides on the filaments may be 100/cm or greater.

In another general embodiment, the position-addressable array of different-sequence oligonucleotides is formed on a planar substrate having a two-dimensional array of regions, each carrying a different-sequence oligonucleotide in said combinatorial library. The density of oligonucleotides on the array is preferably 1000/cm$^2$.

For use in constructing a position-addressable array of long, typically biological gene probes, e.g. cDNAs, cloned genomic fragments, and expressed sequence tags (ESTs), the method may further include the steps of contacting the probe array formed above with a second set of gene-probe templates whose members each have a probe-recognition segment whose sequence is complementary to a selected, known-sequence gene probe segment in the existing probe array, and a gene segment which is complementary to a selected gene sequence. The contacting is carried out under complementary-strand hybridization conditions such that each member in the second set of templates becomes hybridized, through its probe-recognition segment, to a complementary-sequence gene probe in the probe array.

The oligonucleotides in the probe array are then extended, by strand-directed polymerization, along the extended gene segment of templates hybridized to the oligonucleotides, to produce the desired gene-probe array.

In another aspect, the invention includes a position-addressable gene array device formed in accordance with this method. The device includes a substrate having a linear or planar array of regions, and a different-sequence gene probe attached to each array region, through a known-sequence oligonucleotide segment which has a unique, known, combinatorial sequence associated with a given array region. The oligonucleotide segments in the array preferably form a combinatorial library of different-sequence oligonucleotides having a selected length of between 3 and 10 subunits, and the different-sequence gene probes preferably include at least 10, and up to several hundred or more nucleotide subunits.

As above, the position-addressable array of different-sequence oligonucleotide segments may be formed on a wound or extended filament having a one-dimensional array of regions, each carrying a different-sequence oligonucleotide segment, preferably at a linear density of different-sequence segments of at least about 100/cm.

Alternatively, the array of different-sequence oligonucleotide segments may be formed on a planar substrate having a two-dimensional array of regions, each carrying a different-sequence oligonucleotide segment, and at a preferred density of at least 1000/cm$^2$.

These and other objects and features of the invention will become more fully apparent when the following detailed description of the invention is read in conjunction with the accompanying drawings.

BRIEF DESCRIPTION OF THE DRAWINGS

FIGS. 4A and 4B illustrate the first and last reaction steps in attaching nucleotide bases to different segments of a filament winding on a second spool whose side dimension is four times that of the spool shown in FIGS. 2A and 2B;

FIG. 5 shows a portion of the nucleotide sequence formed on the filament after nucleotide addition reactions, such as illustrated in FIGS. 4A and 4B;

FIGS. 6A and 6B illustrate the first and last reaction steps in attaching nucleotide bases to different segments of a filament winding on a third spool whose side dimension is four times that of the spool shown in FIGS. 4A and 4B;

FIG. 7 shows a portion of the nucleotide sequence formed on the filament after nucleotide addition reactions, such as illustrated in FIGS. 4A and 4B;

FIGS. 8A–8D illustrate successive nucleotide addition reactions suitable for filament-based synthesis of oligonucleotides having free 3' ends;

FIG. 9 illustrates a portion of a planar oligonucleotide array that may be employed in the invention;

FIG. 10 shows two oligonucleotides, $O_n$ and $O_{n+1}$, in an oligonucleotide library formed on a multi-sided spool, as illustrated in FIGS. 1–7;

FIG. 11 shows two gene probes, $P_n$ and $P_{n+1}$, in a mixture of gene probes to be contacted with an oligonucleotide array having representative sequences shown in FIG. 10, in forming a position-addressable array of gene probes in accordance with the invention;

FIGS. 12A–12D illustrate steps in forming a gene probe array from the oligonucleotide array illustrated in FIG. 10 and the gene probes illustrated in FIG. 11; and FIGS. 13A–13D illustrate steps in forming an extended gene probe array from the probe array illustrated in FIG. 12D and a mixture of extended gene-probe templates.

DETAILED DESCRIPTION OF THE INVENTION

I. Definitions

Figure 1:
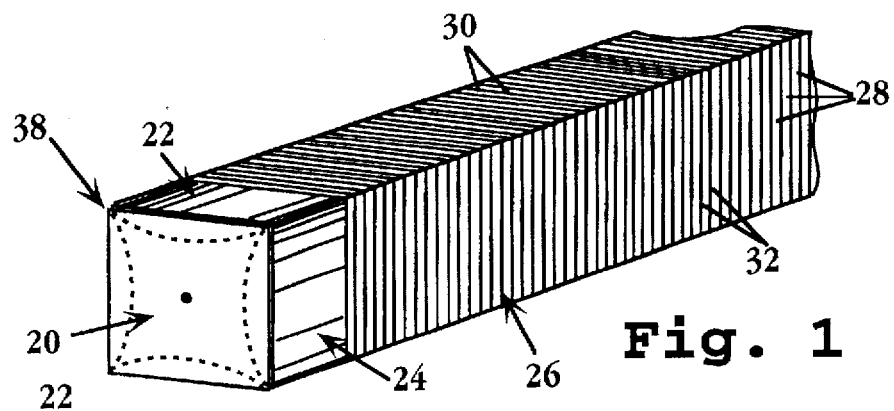
FIG. 1 is a fragmentary perspective view of a spool used in forming a position-addressable oligonucleotide array, for use in preparing a position-addressable gene probe array in accordance with one embodiment of the invention.

The terms below have the following meanings, unless indicated otherwise:

"Oligonucleotides" refers to nucleotide oligomers nucleotides containing typically between about 3 and 50 nucleotide subunits. In the context of oligonucleotides attached at their 5' ends to an array support, in a position-addressable oligonucleotide array, the subunits forming the oligonucleotide may include or be composed primarily of nucleotide analog subunits, or other subunits capable of forming sequence-specific Watson-Crick base pairing, when assembled in a linear polymer, with the proviso that the free ends of the oligonucleotides are ribonucleotide or deoxyribonucleotide subunits capable of providing a suitable substrate for strand-directed polymerization in the presence of a DNA polymerase and one or more nucleotide triphosphates, e.g., conventional deoxyribonucleotides with free 3' OH groups.

A "known-sequence oligonucleotide" is an oligonucleotide whose base sequence in known.

A "gene probe" is an oligonucleotide or polynucleotide which has a base sequence complementary to that of a region of a gene, genomic fragment, cDNA, messenger RNA, expressed sequence tag (EST) or other known-sequence nucleic acid, where the region of complementarity is typically between 10 to 100 or more bases, and the gene probe itself is preferably 10–50 or more bases.

A "position-addressable array of different-sequence oligonucleotides or probes" refers to a linear or planar array of oligonucleotides, each oligonucleotide having a different, known, unique sequence associated with a known location (address) in the array.

A "combinatorial library of oligonucleotides" is a set of oligonucleotides containing substantially each sequence permutation that can be formed by placing a selected one of a number of different subunits at each of a selected number of residue positions. These residue positions may be contiguous or may be interrupted by one of more residues filled with a single subunit (or subunit sequence) only.

A "combinatorial sequence" refers to one of the possible permutation sequences in a combinatorial library of oligonucleotides.

A "high-density array" of oligonucleotides, probes, or gene fragments (regions) refers to a linear array of at least 100 regions/cm, or to a planar array of at least 1,000 regions/cm$^2$.

"Complementary-strand hybridization conditions" refer to temperature, ionic strength and/or solvent conditions effective to produce sequence-specific hybridization between an single-stranded oligonucleotide and its complement-sequence nucleic acid strand. Such conditions are preferably stringent enough to prevent hybridization of two nearly-complementary strands that have one or more internal base mismatches.

"Strand-directed polymerization" refers to nucleic acid strand extension, in the presence of a suitable DNA or RNA polymerase, and all four deoxynucleotide triphosphates, of primer strand hybridized to a template strand, where the sequence of bases in the template strand directs the sequence of bases added in the primer strand.

II. Producing Position-Addressable Oligonucleotide Arrays

This first section describes linear and planar oligonucleotide arrays useful in practicing the invention. The linear array is formed according to the steps detailed in co-owned U.S. patent application Ser. No. 08/512,027 for Method and Apparatus for Producing Position-Addressable Combinatorial Libraries, filed Aug. 7, 1995 and incorporated herein by reference. The method is outlined below with respect to FIGS. 1–8. A planar oligonucleotide array, such as the array shown fragmentarily in FIG. 9, may be constructed according to known methods (e.g., Pirrung, Southern).

Considering the construction of a high-density linear array of oligonucleotides, FIG. 1 shows a spool 20 having a square cross-section defining four equal axially extending surface regions, such as regions 22, 24. A filament 26 wound on the spool has multiple windings, such as windings 28, each encircling the spool one time. The spool partitions each winding into four equal segments, such as segments 30 extending across the upper surface of the spool in the figure, and segments 32 extending across an adjacent spool surface. It will be appreciated that the segments disposed over any given spool surface region, e.g., segments 30, are regularly spaced segments of the filament, with such in an extended, linear form. In the present case, such segments have a length W corresponding to the width of each surface region on the spool, and are separated by 3×W length intervals.

Each group of segments is reacted sequentially with one of a plurality of selected reagents, to chemically attach a selected nucleotide subunit to the segments in each surface region, such as discussed below with respect to FIGS. 8A–8D.

After the above reaction steps, the filament is wound on a second spool having a plurality of axially extending surface regions whose widths are preferably four times that of the first spool, or one-quarter that of the previous spool, if he stepwise subunit addition is performed on successively smaller spools (see below). The filament winding operations and spool-surface reaction steps are continued until the desired oligonucleotide library is formed.

To determine the number and sizes of spools to be used, it is useful first to determine the total number of subunit addition steps required and the order in which the addition steps will be carried out. As an example, it will be assumed that the desired library is to be formed by a series of six subunit-position addition steps, where the total number of different-sequence compounds in the library will be $4^6$, or 4,096. Four separate reagents will be used per subunit addition step; therefore, four-sided spools will be used. The final (smallest) spool containing this library will have 4,096/4=1,024 windings. Assuming a filament thickness of 15 microns, and a 5 micron inter-winding spacing, the total displacement of the wound filament upon the spool will be 1,024×20 microns, or about 2 cm.

In order to limit the total filament length, it is desirable to place these 1,024 windings on a spool having a small side dimension, but sufficient to prevent spool bending over the spool length, e.g., 2 cm, of the windings. In the present case, a metal spool, e.g., stainless steel spool, having a square I-beam or crossbar configuration, and a side dimension of 0.5 mm is selected. The total length of the filament used is then 1,024×0.5 mm×4 (sides), or about 2 m. The final library density will be about $4 \times 10^3 / 2 m$, or about 200/cm.

Table 1 below shows the diameters of the spools used in constructing a library having this filament length and thickness and numbers of filament windings, starting with the smallest spool. The last synthesis step, involving attaching four nucleotides to four 0.5 m segments of the filament, does not involve reaction on a spool.

TABLE 1

| Step | # of Members | Width per Side |
|---|---|---|
| 1 | 4 | 500 microns |
| 2 | 16 | 2 mm |
| 3 | 64 | 8 mm |
| 4 | 256 | 3.2 cm |
| 5 | 1,024 | 12.8 cm |
| 6 | 4,096 | approx. 0.5 m (not wound) |

The filament employed must be of a material that, at dimensions in the 15 micron range, will be highly flexible and of high tensile strength to prevent stretching during filament winding on different-size spools. In one preferred embodiment, the filament is a metal wire, typically 2–25 microns in diameter, coated with a thin suitable polymer coating, e.g., 0.5–2 micron coating thickness. Suitable wires of these dimensions formed of copper, platinum, platinum-iridium alloy (U.S. Pat. No. 5,201,903), or stainless steel are known.

Suitable polymers for the coating are polystyrene, polypropylene, nylon, polyacrylamide, PVC, and the like. Methods for forming thin polymer coatings, e.g., 0.5–2 microns coating thickness, on a metal substrate are known (Lee, Coeling, and U.S. Pat. Nos. 5,201,903 and 5,137,780). Such methods include spray coating (Coeling), vacuum deposition and various methods of in situ polymerization directly onto the wire (Lee). Such methods of in situ polymerization include glow discharge polymerization, electron beam polymerization, and photopolymerization, the last of which has been used to form ultrathin coatings of <0.1 micron.

Preferably, the polymer is applied to the wire in an uncrosslinked state and is then irradiated to lightly crosslink the resin coating, thus reducing swelling during the reaction steps of the method. Irradiation crosslinking is primarily effective with polyolefins, such as polystyrene, polybutadiene, and polypropylene. The use of functionalized polystyrene resins for solid state synthesis is well established, and polypropylene has been reported as a useful substrate for oligonucleotide synthesis (Matson, et al.).

For purposes of illustrating the method, the reaction order will be from smaller to larger spools. In actual practice, it is generally preferred to carry out the reactions in the reverse order, so that the final reaction is carried out on the smallest spool, which then forms the library device that can be used for preparing gene probe arrays in accordance with the invention (Section III).

Figures 2A, 2B:
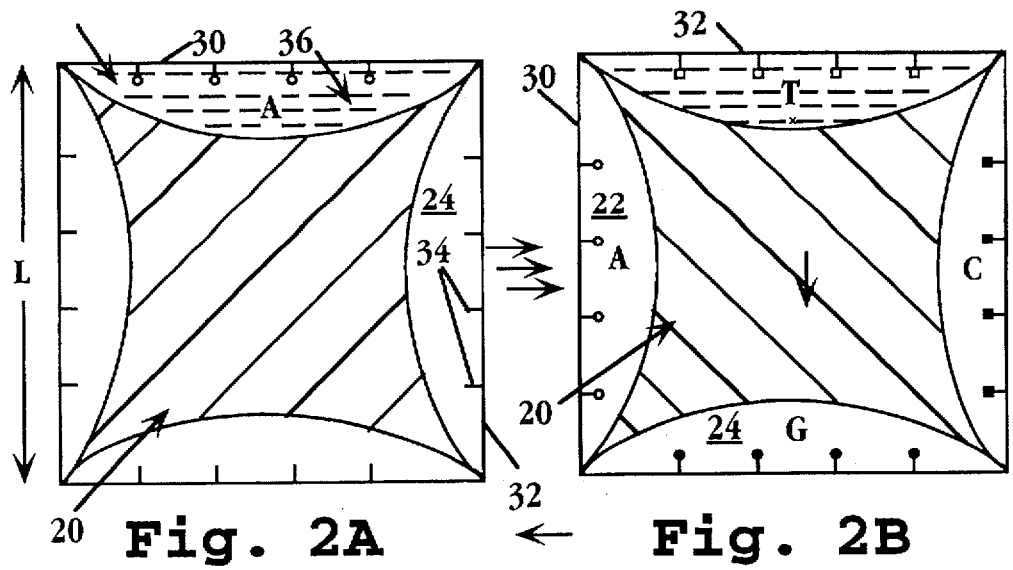
FIGS. 2A and 2B illustrate first and last reaction steps in attaching four nucleotide bases to different segments of a filament winding on the spool in FIG. 1.

FIGS. 2A and 2B illustrate attachment of the first sequence of nucleotide bases to the filament, where the features in the figure have the same numbers as in FIG. 1. Linkage sites on each filament winding segment are indicated by tick marks, such as marks 34 on segment 32. Although the tick marks are shown on one side of each winding segment, it is understood that the linkage sites are present on all sides of the filament segments.

As will be seen below, these linkage sites preferably include a linker used in attaching the growing oligonucleotide chain to the filament, where the linker itself may include at its free end, a fixed-sequence oligonucleotide segment, such as described below with respect to FIGS. 10 and 11. This pre-library sequence is used to optimize probe hybridization specificity and stability with a library sequence, as discussed below.

As a first step in the synthesis of the library oligonucleotide, the filament segments associated with region 22 in the spool are reacted with a reagent solution of a 3'-protected adenosine nucleoside, which is added to the channel, indicated by 36, formed by region 22, and closed at opposite spool ends by end plates, such as plate 38 seen in FIG. 1.

Although the reagent is shown added to the level of the winding segments in the figures, it will be understood that the reagent solution is preferably added to a level forming a positive meniscus, such that all sides of the windings segments are bathed in the solution, and this consideration applies to all of the subunit or substituent addition reactions described below.

The reaction is effective to add the selected nucleoside, e.g. deoxyadenosine (A), to the filament at the linkage sites, where such sites include a linker designed for reacting with the unprotected 5'-OH group of the added nucleotide, for example, where the linker terminates in a 3' phosphoramidate activated nucleoside.

The subunit addition reaction is then repeated successively for each of the three remaining reaction regions, to successively attach the selected nucleosides deoxyguanosine (G, closed circles), deoxycytidine (C, closed squares) and deoxythymidine (T, open squares) to each of different groups of filament segments, as indicated in FIG. 2B. The resulting filament contains the sequence of nucleosides shown in FIG. 3, where each nucleotide is attached to periodically recurring segments of length L (the width of a spool side), and the four nucleosides form a repeating sequence of length 4L on the filament.

As will be seen in FIG. 8, the newly added nucleosides are 3'-protected during the linkage step. The protecting groups must be removed and the 3'-0H group activated to enable reaction with the next series of 5'-free OH nucleotide subunits. The deprotection and activation steps may be carried out with the filaments still wound on the first spool, with the filament unwound, or after winding the filament on the second spool.

Figure 3:
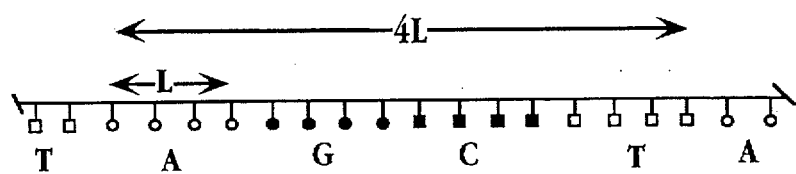
FIG. 3 shows a portion of the nucleotide sequence formed on the filament after the reactions shown in FIGS. 2A and 2B.

With reference to FIGS. 4A and 4B, the filament is now wound on a second spool 40, which, in the illustrated example, has a width 4L, corresponding to the length of the repeating sequence of four nucleosides in FIG. 3. For example, from the spool sizes given in Table 1, the first spool may have a width L of 500 microns, and the second spool a width 4L, or 2 mm. The number of windings on the second spool is consequently ¼ the number of first-spool windings, and the displacement of the windings on the spool may be proportionately less.

As above, spool 40 defines four channels, such as channels 42 and 44, which are used to hold the reagents used in attaching the second series of nucleotide subunits to the filament segments. As shown in FIG. 4A, each complete sequence formed in the first-spool reaction steps is contained in each of a multiplicity of segments associated with a single region, such as region 46, disposed over a single side on the second spool. As illustrated in FIGS. 4A and 4B, the 3'-activated segments in each region are successively exposed to reaction with one of the four 3'-protected nucleoside reagents, to add each of these nucleosides to the segments in each region, as indicated, following the general reactions steps discussed above.

The resulting filament has the nucleotide sequence shown in FIG. 5. Each repeating sequence is now of length 16L and consists of all possible permutations ($4^2$) of dimers based on the four nucleotide bases.

The filament is then wound on a third spool 48, which, in the illustrated example, has a width 16L, corresponding to the length of the repeating sequence of 16 nucleotide dimers in FIG. 5, e.g., 8 mm in Table 1. Again, each complete sequence formed in the previous reaction is contained in the multiplicity of filament segments disposed over each region, such as region 50, defined by each face of the third spool.

After removal of the 3'-protecting groups in the terminal subunits, and activation of these 3'-groups, the segments disposed over each region are successively exposed to a reactive solution of each of the four 3'-protected nucleosides, as described above. The reactions are effective to add each nucleoside to each of the 16 dimers, represented by X's in FIGS. 5 and 6A–6B, attached to the filament segments associated with each region, such as region 50 in FIG. 6A.

The resulting filament has the nucleotide sequence which is partially shown in FIG. 7. Each repeating sequence is now of length 64L and consists of all possible permutations ($4^3$) of trimers based on the four nucleotide bases. FIG. 7 primarily illustrates the portion of this sequence, 16L in length, which has A as its third nucleotide. It will be appreciated that repeating groups of 16 dimers will have each of the four different nucleotides at the third position, collectively forming the 64 different trimer sequences that repeat themselves along the length of the filament.

These steps are repeated with the increasing-size spools, such as the two additional spools indicated in Table 1. In the present example, this leads to a $4^5$-member library, consisting of all possible permutations of pentamers based on the four nucleotide bases.

The final step, leading to a $4^6$-member library, would involve only a single winding, since the extended filament at this stage contains four repeating sequences of pentamers and thus would be wound only once around a spool whose side width would be about 0.5 m. It may be more convenient to carry out this final subunit addition by (i) removing the 5'-protecting groups from the chain-end subunits and (ii) immersing each of the four segments of the filament, each containing a complete sequence of pentamers, into one of four solutions of activated, 5'-protected nucleotide subunits (A,C,G, and T, as in the previous steps).

The resulting filament will contain a single sequence of hexamers making up a $4^6$-member library and containing all possible permutations of hexamers based on the four nucleotide bases. According to an important feature of the method, the sequence at each position along the filament, whether in linear or wound form, is known from the steps employed in library synthesis. By way of example, if the $4^6$-member oligonucleotide library above is constructed in a larger-to-smaller spool direction, and always in the order of subunit addition A, G, C, T, the first quarter segment of the filament position would contain A at the first subunit position, the second quarter segment, G at this position, and so on. Within each of these quarter segments, the first quarter subsegment would contain an A at the second subunit position, the second quarter subsegment, G at the second subunit position, and so on. At the final smallest-spool, the final (sixth) subunit added would of course be the particular subunit added at each of the spool's surface regions.

FIG. 8 shows one exemplary synthetic scheme used for preparation of the library of oligonucleotides on a resin-coated filament, in accordance with the invention. In FIGS. 8A–8D, the filament is indicated fragmentarily at 51, and includes a metal wire core 52 encased in a thin polymer coating 54.

The polymer coating is derivatized, conventionally, with a linker 56, to which the first nucleotide subunit (or a pre-library subunit) is then attached via its 5' OH end. The linker molecules are preferably of sufficient length to permit the compounds in the completed library device to interact freely with probe sequences to which the device is exposed in forming the probe array of Section III. Longer linkers are also known to lead to more efficient nucleoside coupling reactions (Gait, p. 45).

The linkage in the present example may be formed by (i) reacting the coated polymer, e.g., a chloromethylated polystyrene, or chlorinated polypropylene (Matson; Chu) with a long chain bifunctional reagent such as a diol, diamine, ethylene glycol oligomer or amine-terminated ethylene glycol oligomer; and (ii) reaction of the free hydroxyl or amino end of the linker with the first nucleoside (or a pre-library nucleotide or sequence), whose 5'-hydroxyl has been converted to a suitable leaving group such as a mesylate, and which is protected in its 3' position with a suitable protecting group, e.g., phenoxyacetyl (Pac) (Virnekas) and also base-protected. After coupling to the linker, the 3' OH group of the newly added nucleotide is then deprotected, e.g., by reaction with $NH_3$ in MeOH, and activated with MeOP($N^iPr_2$)Cl in $EtN^iPr_2$, using standard procedures (Virnekas), and as illustrated in FIGS. 8A and 8B.

The phosphotriester will be converted to a phosphate linkage after oligonucleotide synthesis is complete. Also, the substrate-to-oligonucleotide linkage is base stable, and the oligonucleotides will thus remain bound to the substrate throughout the deprotection steps which conclude the synthesis. This issue has been addressed by Southern and Matson, inter alia.

After 3'-deprotection and activation at the 3' OH group, a second 3'-protected nucleoside (e.g., deoxyguanosine) is added, giving the dimer AG sequence (FIG. 8C) after oxidation. These steps are repeated with further nucleoside units (FIGS. 8C and 8D) until the desired oligonucleotides have been formed on the filament. At this point, the terminal 3'-hydroxy groups are deprotected, and activated, as above, except that the terminal nucleotide is left in a free 3'-OH form. Finally, the methyl groups on the phosphotriester linkages are removed by treatment with thiophenol or ammonia, and the purine and pyrimidine bases are deprotected, e.g., by treatment with ammonia, all according to known methods (e.g., Gait).

Each nucleoside added in the synthesis is 3'-protected, preferably by a phenoxyacetyl (Pac) group. The exocyclic amino groups on the purine and pyrimidine bases of the nucleosides are also protected, as amides, throughout the sequence, according to well established methods (Gait), and can be deprotected by treatment with ammonia upon completion of the library synthesis. Because the coupling reactions are sensitive to air and moisture, they are preferably carried out under an inert atmosphere.

The members of the oligonucleotide library illustrated above consist of a sequence of single deoxyribonucleotides. Alternatively, the subunits forming the library may be dinucleotides, trinucleotides, or higher order oligonucleotides. For example, at each subunit addition step, one of typically 4–20 different trinucleotide "subunits" corresponding to one of up to amino acid codons, could be added at each subunit addition step (Virnekas).

FIG. 9 shows a fragmentary portion of a position-addressable planar array 60, having a support substrate 62 defining a plurality of discreet array regions, such as regions 64, 66. Each region supports attached molecules of an oligonucleotide having a known sequence, and the oligonucleotides collectively form a combinatorial library of nucleotide sequences, each being associated with a known address or region of the array.

The oligonucleotides on the array are preferably 3–10 nucleotides subunits in length (where "subunit" refers to single or multiple-nucleotide units), and are attached to the substrate through a linker, similar to the attachment of oligonucleotides to a filament substrate. Methods of forming high-density oligonucleotide arrays of this type have been described, e.g., Pirrung, U.S. Pat. No. 5,143,854 and Southern, EP Patent No. 373,203 (1994). The step-wise nucleotide addition reactions described in these references may have to be modified for synthesis in a 5' to 3' direction, employing, for example, the approach discussed with reference to FIG. 8.

III. Producing Position-Addressable Probe and Gene Arrays

In forming a position-addressable array of gene probes, in accordance with the present invention, a position-addressable array of the oligonucleotides described above is contacted with a set of gene-probe templates, where each template set has a probe segment whose sequence is complementary to a selected, known-sequence gene probe and a recognition segment whose nucleotide sequence is complementary to one of the oligonucleotides in the array. This contacting is carried out under complementary-strand hybridization conditions such that each template becomes hybridized, through its recognition segment, to a complementary-sequence oligonucleotide in the array of oligonucleotides. The oligonucleotides in the array are then extended, by strand-directed polymerization, along the probe segments of the templates hybridized to the oligonucleotides, to produce the desired probe array.

FIG. 10 shows a fragmentary cross sectional portion of a spool 68 and a segment 70 of a filament in a spooled filament of the type shown in FIG. 1. The filament segment shown includes two sides 70a, 70b of a four-sided winding, where each of the four sides of each winding has attached combinatorial oligonucleotides which differ from one another in one sequence position—in this case, in the terminal 3' position. The oligonucleotide molecules $O_n$ in side 70a in the figure include three fixed "pre-library" sequences 5'-TTA-3', which are provided on a linker in the filament, prior to library sequence construction, and six nucleotides 5'-ACCGGC-3' which form one of the 4096 possible six subunit permutations of four single nucleotides. Similarly, the oligonucleotide molecules $O_{n+1}$ attached to the side 70b of the segment include the three fixed "pre-library" sequences and six nucleotides 5'-ACCGGT-3' which form another one of the 4096 possible six subunit permutations of the oligonucleotide library.

The purpose of three pre-library sequences is to provide a total of at least 9–10 nucleotides in the oligonucleotides for hybridization with complementary regions of a gene-probe template, thus improving the specificity of the hybridization and increasing the temperature at which base-specific hybrids will stably form (e.g., Hames, and Sambrook, 11.8). These advantages may also be achieved by using, for example, di- or trinucleotides as the library subunits, so that a six-subunit library contains 12 or 18 nucleotides, respectively.

Two members of a set of gene-probe templates are shown at 72, 74 in FIG. 11, and designated $P_n$ and $P_{n+1}$, respectively. Each template in this set, such as template $P_n$, contains a 3' nine-nucleotide recognition segment 72a whose nucleotide sequence is complementary to one of the oligonucleotides in the array—in this case oligonucleotide $O_n$—and a twelve-nucleotide probe segment 74b whose sequence is complementary to a selected, known-sequence 12mer gene probe to be included in the array. The second template shown, $P_{n+1}$, similarly has a recognition sequence that is complementary to $O_{a+1}$, and a probe segment that is complementary to a second, different gene probe to be included in the array.

The set of templates can be synthesized by conventional solid state oligonucleotide synthesis methods (Gait), where each member of the set is individually synthesized and purified, then combined in preferably equimolar amounts to form the template set.

For a 4096-oligonucleotide array, the template set may contain up to 4096 different gene-probe segments, although fewer total gene sequences, with some gene-sequence duplications at selected library positions may be desirable, e.g., for internal control.

The templates are contacted, i.e., placed in solution in the presence of, the oligonucleotides of the array, under conditions that lead to hybridization between the recognition segments of the templates and complementary array oligonuclotides. The hybridization conditions are preferably stringent (high-criterion) conditions in which only hybrids with a high degree of homology form. Typical high criterion conditions are about 8° C. lower than the melting temperature $T_m$, (Hames, p. 108). Thus, for example, in the case of 9mer hybrids, where a melt temperature of about 40° C. may be expected, a high-criterion annealing or hybridization temperature may be about 32° C.

FIGS. 12A–12D illustrate the steps in forming a probe array in accordance with the invention, where the figure numbers and the oligonucleotide sequences designated $O_n$, $O_{n+1}$, $P_n$, and $P_{n+1}$, are the same as in FIGS. 10 and 11. Contacting an oligonucleotide array (FIG. 12A) with a set of gene-probe templates under suitable hybridization conditions, as above, leads to sequence-specific attachment of the probes in the set to position-addressable oligomers in the array, as illustrated in FIG. 12B, with the gene-probe segment in each probe extending beyond the 3' end of the associated array oligomer. The oligonucleotides attached to the array are now extended by strand-directed polymerization along the associated gene segments, to produce the double-stranded gene probes indicated in FIG. 12C. Suitable polymerization conditions in the presence of a DNA polymerase, e.g., Klenow fragment of $E.$ $coli$ DNA polymerase I, T4 DNA polymerase, T7 polymerase, and all four nucleotide triphosphates (NTP's), are well known (e.g., Sambrook, 5.35–5.51).

In general, under the high-criterion hybridization conditions that can be selected, any internal base mismatch will prevent formation of a stable duplex. Further, a mismatch at the 3' terminus of the oligonucleotide may block successful strand-directed polymerization, thus limiting strand extension to exact basepair matches between the array oligonucleotides and template recognition segments.

As a final step, the double-stranded probes in the array may be denatured, e.g., by heating above the $T_m$ of the probe, and the template strand released, as indicated in FIG. 12. The final probe array, indicated at 76 in FIG. 12D, includes a substrate spool 68, having a linear array of regions, such as regions 70a, 70b, where each of the regions has a different-sequence gene probe fragment attached thereto. The gene probes are attached to each region through an oligonucleotide segment (corresponding to the original array oligonucleotide), where these segments have a unique, known, combinatorial sequence of nucleotide subunits associated with a known-position array region, and collectively form a combinatorial library of sequence permutations. The gene-probe segments in the array are at least 10 bases in length, and typically, 15–50 bases.

In the gene-probe embodiment just described, the set of template oligonuclotides employed are readily synthesized by solid-phase methods. Such methods may be difficult to apply, however, where the gene-probe segments correspond to genomic fragments, cDNA's, EST's or other genetic coding regions with lengths of 50 to several hundred or more bases. In this case, it is advantageous to employ biological synthesis for producing the long gene probe fragments, and rely on relatively short synthetic oligonucleotides for coupling the long segments to the array. This approach is illustrated in FIGS. 13A–13D.

FIG. 13A shows a fragmentary cross-sectional portion of the gene-probe array shown in FIG. 12D, where the gene-probes in the array, indicated at $P_n$ and $P_{n+1}$, have the sequences shown in FIG. 11. In this case the probe segment in each region of the array is complementary in base sequence to the 3'-end region sequence in one of a set of large gene-probe templates, such as those designated $F_n$ and $F_{n+1}$. As already indicated, the large gene probes are preferably produced biologically, typically as closed genomic, cDNA or EST fragments. The 3'-end region of the large gene-probe templates that are complementary to the gene-probe segments on the already-formed gene probe array are also referred to herein as recognition sequences. Preferably these are 15 bases or more in length, to provide good hybridization specificity with the array gene probes.

Thus, to practice this embodiment of the invention, it is only necessary to know the base sequence of each recognition segment in the large gene-probe templates, although typically the sequences of large contiguous regions of 100 or more bases will be known.

The method for forming a long gene-probe arrays closely follows that discussed above with respect to FIGS. 12A–12D. Briefly, a set of long gene-probe templates, each having a recognition segment complementary to the probe segment of an oligonucleotide probe array is contacted with the array, under preferably high-criterion hybridization conditions. Where, for example, the array-probe segment has 20 bases of complementarity with the recognition segment of the gene-probe templates, and an average $T_m$, of about 60°–70° C., the hybridization temperature should be 52°–62° C.

The contacting step is effective to hybridize each long gene probe template, e.g. $F_n$ and $F_{n+1}$, with a corresponding known-position probe recognition sequence, as indicated in FIG. 13B. These templates now provide for strand-directed polymerization in the presence of a suitable polymerase and NTP's, as above, to form the double-strand long gene probes shown in FIG. 13C. As a final step, the array have treated to remove template strands, as above.

The resulting probe array, indicated at 78 in FIG. 13D, includes a substrate spool 68, having a linear array of regions, such as regions 70a, 70b, where each of the regions has a different-sequence gene probe—in this case, of up to several hundred bases in length—attached to that region through an oligonucleotide segment (corresponding to the original array oligonucleotide), where these segments have a unique, known, combinatorial sequence of nucleotide subunits associated with a known-position array region, and collectively form a combinatorial library of sequence permutations.

IV. Utility

The gene probe arrays of the invention have a variety of uses in sequencing-by-hybridization (SBH), diagnostics, and gene-expression studies.

As an example in the diagnostics area, the gene probes in the array can represent sequences corresponding to a number of different known mutations in a selected gene, e.g., the cystic fibrosis gene, where each different mutation is associated with a known addressable region of the array.

To test for a particular mutation in a DNA sample, a DNA sample is first labeled, e.g., with a fluorescent label, then reacted with the probes in the array under high-criterion hybridization conditions. Examination of the array, e.g., by fluorescence microscopy, is then used to identify gene probes where binding has occurred. Knowing the position of the labeled array region, the exact mutation in the sample can be determined. A large array can of course be designed to carry multiple gene types, each having several different possible mutations.

In the area of gene expression studies, labeled cDNA's from a cell or cell type in a given state can be reacted with a large cDNA-library array prepared as above, to determine which of the cell genes are being expressed and at what levels, for purposes of, for example, (i) monitoring changes in gene expression during a treatment, or (ii) identifying library cDNA's which are associated with changes in cell state or cell type.

Although the invention has been described with respect to particular spool structures, methods, libraries, and library devices, it will be appreciated that various changes and modification can be made without departing from the invention.

It is claimed:

1. A method of producing a position-addressable array of known-sequence gene probes, comprising (i) contacting a position-addressable array of different-sequence oligonucleotides where each oligonucleotide in the array has a unique known combinatonal sequence with a known-address region in the array, and (ii) and a free, 3' oligonucleotide end, with a set of single-stranded gene-probe templates, where each member of the set has a 5'-end probe segment whose sequence is complementary to a selected, known-sequence gene probe and a 3'-end recognition segment capable of hybridizing selectively to one of the oligonucleotides in said array, under complementary-strand hybridization conditions, said contacting being carried out under complementary-strand hybridization conditions such that each member in said set of templates becomes hybridized, through its recognition segment, to one of the oligonucleotides in the array of oligonucleotides, and (ii) extending the oligonucleotides in the array, in a 3'-to-5' direction, by DNA polymerization, where the oligonucleotides in the array serve as primers, and the 5'-end gene probe segments in the gene-probe templates, as templates for primer extension, to produce a position-addressable array of double-stranded gene probes.

2. The method of claim 1, wherein the probe segments in the set of templates are at least 15 nucleotide bases in length.

3. The method of claim 1, wherein the oligonucleotides in said array form a combinatorial library of different-sequence oligonucleotides having a selected length of between 3 and 8 nucleotide bases.

4. The method of claim 3, wherein said position-addressable array of different-sequence oligonucleotides is formed on a wound or extended filament having a one-dimensional array of regions, each region carrying a different-sequence oligonucleotide in said combinatorial library.

5. The method of claim 3, wherein said position-addressable array of different-sequence oligonucleotides is formed on a planar substrate having a two-dimensional array of regions, each region carrying a different-sequence oligonucleotide in said combinatorial library.

6. The method of claim 1, for use in constructing a position-addressable array of gene probes that are each at least 50 bases in length, which further includes the steps of (iii) denaturing said double stranded gene probes formed in step (ii) to release the template strand thereby forming a single stranded gene probe array and; (iv) contacting the single stranded gene probe array formed in step (iii) with a set of gene-probe templates whose members each have a 3'-end probe segment capable of hybridizing selectively, under complementary-strand hybridization conditions, to a selected, known-sequence gene probe in the probe array, and a 5'-end extended gene segment which is complementary to a selected gene sequence, said step-(iii) contacting being carried out under complementary-strand hybridization conditions such that each member in said set of gene templates becomes hybridized, through its probe segment, to a complementary-sequence probe in the probe array, and (iv) extending the probes in the array, in a 3'-to-5' direction, by DNA polymerization, where the gene probes in the array serve as primers, and the 5'-end extended gene segments in the gene-probe templates, as templates for primer extension, to produce a position-addressable array of such gene probes wherein said gene probes are at least 50 bases in length.

7. A position-addressable gene array device comprising a substrate having a linear or planar array of regions, each of said regions having a known different-sequence gene probe segment attached thereto, where each gene probe segment has a length of at least 10 bases, and is attached to the substrate, at its 5' end, to the 3' end of an oligonucleotide segment attached to the array substrate, where the oligonucleotide segment at each region of the array has a unique, known, combinatorial sequence of at least 3 nucleotide bases associated with a given array region.

8. The device of claim 7, wherein said gene probe segments are at least 50 nucleotide bases in length.

9. The device of claim 7, wherein the oligonucleotide segments in the array form a combinatorial library of different-sequence oligonucleotides having a selected length of between 3 and 10 nucleotide bases.

10. The device of claim 9, wherein said position-addressable array of different-sequence oligonucleotide segments is formed on a wound or extended filament having a one-dimensional array of regions, each region carrying a different-sequence oligonucleotide segment in said combinatorial library.

11. The device of claim 9, wherein said position-addressable array of different-sequence oligonucleotide segments is formed on a planar substrate having a two-dimensional array of regions, each region carrying a different-sequence oligonucleotide segment in said combinatorial library.

12. The device of claim 11, wherein the different-sequence oligonucleotides have a 5' proximal to 3' distal oridentation on said substrate.

13. The method of claim 1 further comprising the step of denaturing said double-stranded gene probes formed in step (ii) to release the template strand, thereby forming a single-stranded gene probe array.

* * * * *